United States Patent [19]

Sharma et al.

[11] Patent Number: 4,929,508
[45] Date of Patent: May 29, 1990

[54] NOVEL DRUG DELIVERY SYSTEM FOR ANTITUSSIVES

[75] Inventors: Shri C. Sharma, Mendham; James J. Shaw, Morristown; Robert K. Yang, Morris Plains, all of N.J.

[73] Assignee: Warner-Lambert Company, Morris Plains, N.J.

[21] Appl. No.: 224,601

[22] Filed: Jul. 26, 1988

Related U.S. Application Data

[60] Division of Ser. No. 701,470, Feb. 14, 1985, Pat. No. 4,797,288, which is a continuation-in-part of Ser. No. 658,101, Oct. 5, 1984, Pat. No. 4,752,485.

[51] Int. Cl.$^5$ ............................................. A61K 47/00
[52] U.S. Cl. ................................. 424/439; 424/440; 424/441
[58] Field of Search ............... 424/439, 440, 441, 450, 424/498; 514/850

[56] References Cited

U.S. PATENT DOCUMENTS

| | | | |
|---|---|---|---|
| 2,808,360 | 10/1957 | Carrara | 514/850 |
| 3,244,588 | 4/1966 | Nielsen | 514/850 |
| 3,456,060 | 7/1969 | Kuhnis et al. | 514/850 X |
| 3,784,702 | 1/1974 | Kimura et al. | 514/850 X |
| 4,427,681 | 1/1984 | Munshi | 514/850 X |

*Primary Examiner*—Thurman K. Page
*Attorney, Agent, or Firm*—Daniel A. Scola, Jr.; Charles A. Gaglia, Jr.; Graig M. Bell

[57] ABSTRACT

A drug delivery system comprising a core material comprising a drug, and a hydrophobic matrix coating the core. The coating delays hydration of the drug and masks the taste of the drug. The coating comprises an emulsifier, an edible fatty acid or wax and a glyceride. The delivery system can be incorporated into various food products, pharmaceutical preparations and proprietary products.

21 Claims, 2 Drawing Sheets

NOVEL DRUG DELIVERY SYSTEM FOR ANTITUSSIVES

This application is a divisional of U.S. Ser. No. 701,470 filed Feb. 14, 1985, now Patent No. 4,797,288 which is a continuation-in-part of U.S. Ser. No. 658,101 filed Oct. 5, 1984 now U.S. No. 4,752,485.

FIELD OF THE INVENTION

The present invention relates to a novel drug delivery system and method of preparation. More particularly this invention relates to a core material having an hydrophobic matrix coating which serves to delay hydration, mask unpleasant taste and protect the drug from such factors as moisture, pH and temperature. The core material comprises a drug.

BACKGROUND OF THE INVENTION

Numerous drugs are known for their unpleasant taste or mouthfeel. The prior art has disclosed products to mask the taste of these drugs, but the products themselves often suffer from unpleasant tastes. Patient compliance with prescribed drug therapies is often low because of this.

The functionality and effectiveness of certain solid drugs such as ion exchange resins is dependent on the active surface area. Fine particles achieve the desired therapeutic effects more effectively than course particles because the former have a higher surface area to weight ratio, e.g., a higher active surface. For example, in the case of ion exchange resins, e.g., cholestyramine, a greater surface area allows enhanced adsorption of bile acids, increased ion exchange, as well as other surface phenomena.

While course drug particles do not have sufficient effective surface area to be as effective as finer drug particles, the finer particles suffer from certain handling, processing, and formulation problems. The finer particles, having a larger total surface are than courser particles, tend to be organoleptically perceived as more bitter or astringent and too dry. These organoleptic characteristics are undesirable. Traditionally, when fine particles were added in therapeutic amounts to a delivery vehicle, e.g., a confectionery formulation, the fine particles tended to disrupt the continuous phase characteristics of the final product.

The prior art has not disclosed efforts to delay hydration of unpleasant tasting drugs. To be effective, coatings must not merely mask the taste, e.g., overcome the unpleasant taste, but also delay hydration of the drug until it passes the oral cavity. Typically, the prior art has focused on water-soluble vehicles, which do not delay hydration of the drug long enough to prevent the unpleasant taste perception.

Additionally, the prior art has not disclosed an effective way of dealing with irregular shaped drug particles, e.g., various morphological structures or surfaces having sharp corners or needlelike projections. Simple conventional mixing techniques have not been completely successful in that the coating was not uniform. Conventional fluidized bed spray coating techniques have also failed to effectively provide a uniform coating on irregular shaped particles. Drug particles which have a low bulk density in addition to being irregularly shaped are particularly hard to uniformly coat with either of these conventional coating techniques. Uniform coatings therefore have been difficult to achieve when the drug particulates had a low bulk densities irregular surfaces, or both. In addition to being uniform, the coatings must be sufficiently flexible to resist cracking during processing.

The instant invention provides a drug delivery system which uniformly coats and protects the drug from moisture and subsequent hydration prior to complete ingestion. The inventive delivery system effectively wets low bulk density drugs as well as drugs having physical structures which are difficult to uniformly coat and provides controlled release of the drug.

The invention provides a method of coating low bulk density, difficult to coat drug particulates as well as providing a coating which protects unstable drugs from destabilizing conditions.

SUMMARY OF THE INVENTION

The present invention concerns a drug delivery system capable of delaying hydration of the drug and masking the taste of the drug comprising:
(a) a drug; and
(b) a hyrophobic matrix comprising
  (i) an emulsifier; and
  (ii) an edible material having a melting point in the range of about 25° C. to about 100 C. selected from the group consisting of
    (a) fatty acids having an iodine value of about 1 to about 10,
    (b) natural waxes,
    (c) synthetic waxes and
    (d) mixtures thereof; and
  (iii) at least one glyceride.

The inventive delivery systems and method of preparation solve the problems associated with surface wetting, uniform coating and delayed hydration encountered with conventional coatings and coating techniques.

The coatings are sufficiently flexible to form protective film barriers without cracking under mechanical forces encountered during application of the coating as well as those stresses present in incorporating the delivery systems into various food products.

The inventive coatings are particularly suitable for drugs which may exhibit instability and subsequent inactivity under high moisture, temperature, pH, reactivity with other ingredients or various other factors.

The inventive delivery systems and compositions are useful in food products such as chewing gums, and other confectionery products, baked goods, pharmaceutical preparations, beverages, tobacco and proprietary products such as toothpaste and mouthwash. Acceptable amounts may vary widely and preferably from about 0.01% to about 100% by weight of the delivery system based on the weight of the final product.

DETAILED DESCRIPTION OF THE INVENTION

The Hydrophobic Matrix

The hydrophobic matrix comprises
(i) an emulsifier; and
(ii) an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; and
(iii) at least one glyceride.

The emulsifier is critical to the hydrophobic matrix and is believed to serve several important purposes. Most importantly, the emulsifier acts as a wetting agent to increase the affinity of the fat or wax to the core material surface. Fat and wax are often not compatible with various surfaces. The emulsifier mediates the poor affinity between these materials and allows for uniform wetting of the drug surface by the fat or wax. Uniform wetting of the surface is critical to proper adherence of the hydrophobic matrix coating and to the effectiveness of the ultimate protection it provides for the drug material.

Secondly, the emulsifier serves as a modifier of the rheological and thermal properties of the fat which lends it the capability of forming an elastic (non-brittle) and flexible film over a wide temperature range. Ordinary fat without the emulsifier would result in a brittle, porous crystalline coating which would be vulnerable to rupture during processing and which would fail to uniformly wet the core material (drug) surface. Additionally, the emulsifier acts to modify the morphological properties of the fat or wax, as well as to increase their heat capacity, thereby retarding liquid to solid phase transitions and allowing for increased flexibility in processing conditions, e.g., the mixture can be processed in a specified temperature range for a longer period of time. The increased heat capacity plays an important role in the final delivery system since more heat will be required before the system melts down and releases the drug material. Thus, at short exposures to elevated temperatures, the delivery system will be more stable than without the addition of the emulsifier.

The high bulk density and high surface area to weight ratio of many drug materials make them generally difficult to coat. The emulsifier increases the viscosity of the fat which facilitates their incorporation. The hydrophilic-lipophilic balance (HLB) values should be in the range of about 3 to about 7. The emulsifier is present in amounts of about 0.5 to about 20% and preferably about 3 to about 5% by weight of the delivery system.

Useful emulsifiers include the reaction product of monoglycerides or sorbitan esters with ethylene oxide (known as polysorbates). Examples of useful polysorbates include sorbitan monostearate, sorbitan monopalmitate, sorbitan monolaurate, propylene glycol monolaurate, glycerol monostearate, diglycerol monostearate, and glycerol-lactyl-palmitate. The preferred emulsifier is lecithin. The *Condensed Chemical Dictionary*, 9th edition, Van Nostrand Reinhold, 1977, defines lecithin as mixtures of diglycerides of fatty acids linked to the choline ester of phosphoric acid. Lecithins are classed as phosphoglycerides or phosphatides. In the instant invention, the lecithin preferably has a minimum of about 95% by weight of phosphatide present. This purity level is generally designated in commercially available lecithins as "95% acetone insolubles." The phrase "95% acetone insolubles" is intended to mean that upon dissolution of the lecithin in acetone, 95% of the lecithin (the phosphatide portion) remains insoluble. Residual impurities such as oil, moisture and soluble non-phosphatides account for the 5% of the materials dissolved and extracted by the acetone. More preferably, the lecithin employed will have 97% insolubles. Additionally, it is required that the emulsifier be soluble in the fatty acid or wax. This is necessary for the emulsifier to perform its various functions described above.

The second required constituent in the hydrophobic matrix coating of the delivery system is an edible material which is itself hydrophobic and which has a melting point in the range of about 25° C. to about 100° C. Those materials useful are selected from the group consisting of fatty acids, natural, synthetic waxes and mixtures thereof. It is important that the melting point be within the recited range since the melting point of the final delivery system product will be greatly affected by the fat or wax constituent.

The term "fatty acid" is meant to include fatty acid-containing materials, e.g., natural fats, but is not intended to be a material identical to the glyceride component.

Those fatty acids which are useful must have an iodine value of about 1 to about 10. The iodine value is a means of determining the degree of unsaturation in fats and oils. The measurement of iodine values are determined by known titrating methods and are reported in terms of centigrams of iodine absorbed per gram of fat and oil sample. (*See Bailey's Industrial Oil and Fat Products*, Vol 2, 4th Ed., Swern, Daniel ed., p 436–438, 1982.) Thus, those fatty acids useful in the inventive systems have an iodine value of about 1 centigram to about 10 centigrams.

Examples of the fatty acids employed are selected from the group consisting of hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil and mixtures thereof.

Those waxes which are useful include natural waxes such as animal waxes, vegetable waxes, petroleum waxes and synthetic waxes having a melting point within the range of about 25° C. to about 100° C. and being edible. Specific examples of waxes which fall within these categories are beeswax, lanolin, bayberry, sugar cane, candelilla, carnauba, paraffin, microcrystalline, petrolatum and carbowax. Mixtures of these waxes may be used as well as mixtures of the waxes with the fatty acids.

The edible fatty acid or wax materials are employed in the instant delivery systems in amounts of about 61% to about 95% by weight of the delivery system, preferably in amounts of about 63% to about 90% and most preferably in amounts of about 66% to about 80%. These amounts are necessary to adequately coat the surface of sweeteners such as aspartame which have a high surface are to weight ratio. Hydrogenated palm oil in the most preferred fatty acid. Paraffin wax and mirocrystalline wax are the preferred waxes.

The edible fatty acid or wax component is critical to the effectiveness of the protective barrier. The hydrophobic matrix, of which the fatty acid or wax is an essential part, provides protection for the core material from heat, light, moisture, pH, reactive chemicals and the like. Additionally, the release of the drug material is controlled via the hydrophobic matrix and can serve other purposes such as the masking of taste for unpalatable or unpleasant tasting materials.

The term glyceride component used herein refers to commonly identified glycerides which are esters of glycerol and fatty acids in which one or more of the hydroxyl groups of the glycerol have been replaced by acid radicals. Mono- and diglycerides are preferred, whereas triglycerides alone are not acceptable.

The mono- or diglyceride component of the hydrophobic coating matrix serves to increase the affinity between the fatty acid or wax and the core material. In addition, for drug materials which are water soluble, the mono- or diglyceride component also serves to help the fat adhere to and wet the surface of the drug. Flexibility and elasticity of the matrix once it forms the film or coating on the drug material is increased due to the glyceride component.

The glycerides are present in amounts of about 0.5 to about 30% by weight of the deivery system. Preferably the glyceride is used in amounts of about 0.5 to about 7% and most preferably about 1% to about 3%. It should be recognized that mixtures of mono- and diglycerides may be used, since most available glyceride materials are mixtures of mono- and diglycerides.

The drugs useful may be selected from a wide range of drugs and their acid addition salts. These materials can be used either singly or in combination in either a single or multiple delivery system. That is, one or more of these materials may be present within one coating matrix or separately coated by the matrix and employed along or in combination in a final product.

Both organic and inorganic salts may be used provided the drug maintains its medicament value and is soluble in the solvent. Exemplary acid salts include hydrochloride, hydrobromide, orthophosphate, benzoate, maleate, tartrate, succinate, citrate, salicylate, sulfate, and acetate.

The weight percent of the drug or its acid addition salt thereof, based on the weight of the coating matrix from about 1% to about 75%; preferably about 5% to about 30%; more preferably about 10% to 20%; and most preferably about 15% to about 19%, which amounts will vary depending upon the therapeutic dosage permitted.

(a) An titussives, such as dextromethorphan, dextromethorphan hydrobromide, noscapine, carbetapentane citrate, and chlophedianol hydrochloride;
(b) Antihistamines, such as chlorpheniramine maleate, phenindamine tartrate, pyrilamine maleate, doxylamine succinate, and phenyltoloxamine citrate;
(c) Decongestants, such as phenylephrine hydrochloride, phenylpropanolamine hydrochloride, pseudoephedrine, hydrochloride ephedrine;
(d) Various alkaloids, such as codeine phosphate, codeine sulfate and morphine;
(e) Mineral supplements such as potassium chloride and calcium carbonates, magnesium oxide and other alkali metal and alkaline earth metal salts;
(f) Laxatives, vitamins and antacids;
(g) Ion exchange resins such as cholestyramine;
(h) Anti-cholesterolemic and anti-lipid agents;
(i) Antiarrhythmics such as N-acetylprocainamide;
(j) Antipyretics and analgesics such as acetaminophen aspirin and ibuprofen;
(k) Appetite suppressants such as phenylpropanolamine hydrochloride or caffeine; and
(l) Expectorants such as guaifenesin.

Additional useful active medicaments include antiinflammatory substances, coronary dilators, cerebral dilators, peripheral vasodilators, anti-infectives, psychotropics antimanics, stimulants, laxatives, decongestants, gastro-intestinal sedatives, antidiarrheal preparations, anti-anginal drugs, vasodialators, antihypertensive drugs, vasoconstrictors and migrane treatments, antibiotics, tranquilizers, antipsychotics, antitumor drugs, anticoagulants and antithrombotic drugs, hypnotics, sedatives, antiemetics, antinauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, anti-uricemic drugs, and the like.

Mixtures of the drugs and medicaments may also be used.

The preferred drugs are cholestyramine and potassium chloride. Cholestyramine is the chloride salt of a basic anion exchange resin which has an affinity for sodium chloride and a particularly strong affinity for acid materials such as bile acids. It occurs as a white powder, insoluble in water and has an amine-like odor and a gritty taste. Cholestyramine is believed to absorb and combine with bile acids in the intestine to form an isoluble complex which is then excreted by the body. Cholesterol is the major precusor of bile acids which are formed by the oxidation of cholesterol. The serum level of cholesterol can be reduced by administration of cholestyramine, which leads to reduction of bile acids and increased oxidation of cholesterol.

The recommended adult dosage of cholestyramine is about 5 to about 50 grams per day; preferably about 12 to about 32 grams per day. Administration is generally about 3 to 4 times daily in dosages of about 2 to 10 and preferably about 3 to 4 grams.

Potassium is a principal cation of intracellular fluid and is believed to be essential for the maintenance of isotonicity and electrodynamic characteristics of the cell. It is also essential for a number of physiologic processes including the transmission of nerve impulses, contraction of cardiac, smooth and skeletal muscles, gastric secretion and normal renal function. Potassium depletion is closely related to the concomitant intake of sodium. High sodium intake causes loss of potassium because of renal Na+-K+ exchange. Numerous causes of potassium depletion are mentioned in the literature, e.g., abnormally high losses due to diarrhea, continuous aspiration of the stomach, decreases in potassium plasma level due to rapid absorption of glucose into tissue (as after administration of insulin) etc. Low plasma levels may bring about weakening of the heart, a fall in blood pressure, muscular weakness and general metabolic dysfunction.

Treatment of potassium and deficiencies can be remedied by administration of potassium salts. Generally potassium chloride is the chosen salt. Potassium chloride is generally sold as a powder or tablet to be dissolved in cold water. Adult dosages are generally about 1.02 to about 2.56 grams (40–100 mEq) per day, administered in amounts of about 50 mEq about 1 or 2 times per day.

The drug is present in the delivery system in amounts of about 50 to about 99% by weight; preferably about 65 to about 85%; and most preferably about 70 to about 80%.

Process of Preparation

The method of preparing the delivery system involves first forming an agglomeration of the core material and the hydrophobic matrix. The agglomerates are then screened to obtain particles of about 200 to about 30 mesh and then coated with one or more layers of hydrophobic material to provide a protective barrier. The agglomerate is formed by mixing at low shear the fatty acid or wax with the glyceride and emulsifier at temperatures of about 75° to about 95° C. until a homogeneous mixture is obtained. The core drug material or combination or core materials are then added to this mixture and mixed at high shear to uniformly dispense the material in the mixture. The dispersion is then fed into a spray nozzle and spray congealed. The term spray congealed as used herein refers to the solidification of the atomized liquid droplets which cool and solidify upon hitting the cooler temperature of the surrounding atmosphere. The nozzle pressure is regulated to control the particle droplet size. The droplets cool and congeal once they are emitted from the nozzle and contact the cooler environment. The result is a dry particle or agglomerate having an approximate eliptical or spherical shape. At this stage, core materials particles are bound together with the hydrophobic matrix, but not adequately coated to fully protect the core material from the environment. The agglomerated particles are then screened to the desired size as mentioned above. The second coating step of the process is now necessary to provide the required protective barrier. Thus, the agglomerate is then coated using standard fluidized bed granulation procedures.

The second coating (e.g., the coating of the agglomerate) may use the hydrophobic matrix. It should be mentioned, however, that the outer coating need not have the emulsifier and glyceride components present since wetting of the core material surface is not critical at this point, having been accomplished in the first coating. Thus, the outer coating need only have the fatty acid and wax components and preferably both. Preferably the outer coating comprises hydrogenated palm oil and paraffin wax in respective amounts of about 61% to about 90% and about 10% to about 40%. The final product is a fine dry particle and is referred to herein as the delivery system. The delivery system preferably has a melting range of about 20° C. to about 90° C. and most preferably a melting range of about 35° to about 38° C., such that it melts and releases the core drug material within the normal body temperature range of humans, having passed through the oral cavity.

As an alternative, but less preferred method, the homogenous mixture of the hydrophobic matrix and core material can be allowed to cool in sheets and subsequently pulverized to a particle size of about 30 to about 200 U.S. standard mesh size (about 600 to about 75 microns). The pulverized particles can then be coated with the hydrophobic mixture using standard fluidized bed coating techniques. An additional alternative method of forming the delivery system comprises spray drying the core material with a known binder such as cellulose or polyvinyl pyrrolidone and the like to form an aggregate. The aggregate is then coated with the hydrophobic coating matrix using conventional fluidized bed coating techniques well known to the skilled artisan. These alternative methods however are not as effective in preparing the delivery systems as the preferred method.

It is important to note that the preferred inventive process involving spray congealing of the liquid hydrophobic coating matrix-core material followed by fluidized bed coating results in a significantly and surprisingly improved coating for protection of the core material. Either spray congealing or fluidized bed coating alone do not provide adequate protective coating of the delivery system and results in premature release of the core material. The congealing step forms an agglomerate of the core material and hydrophobic matrix. The matrix binds together the core particles but only partially coats the core. The core material is "randomly" coated in the sense that it is pure change that the matrix completely coats and enrobes the material particularly if the material is difficult to coat.

Fluidized bed coating is necessary to achieve the uniform coating necessary to protect the core material. For example, with rod-like or needle-like shaped materials, the spray congealing orients the particles into an agglomeration which is significantly easier to coat, e.g, the agglomerate approximates an eliptical or spherical shape (see FIG. 2), which is then easily uniformly coated in the fluidized bed. Fluidized bed coating alone does not provide a uniform protective coating.

The taste masking and delayed hydration characteristics of the delivery system is dependent not only on the completeness of the surface area coated, but on the thickness of the coating. A balance should be maintained such that too thick a coating is not used so as to prevent proper release of the drug. It has been determined that using the exterior coating in amounts of about 200 to about 400% by weight of the agglomerate maximizes the taste masking benefits with the controlled release benefits. Use of the exterior coating in less than amounts of about 30% by weight of the core (drug) material.

The delivery system in its final form is a dry spherical particulate having a U.S. standard mesh size of about 200 to about 30 and preferably about 150 to about 70.

In addition to drugs the delivery system can also be used to protect core materials such as sweeteners, flavoring agents, and the like.

Vehicles

The delivery system in its final form may be referred to as a composite. The composite is useful in a variety of vehicles such as food products, medicaments, baked goods, pharmaceutical preparations, tobacco and proprietary products such as toothpaste and mouthwash, and the like. Once prepared the composite may be stored for future use or formulated with conventional additives, that is, pharmaceutically acceptable carriers and confectionery ingredients to prepare compositions which offer a variety of textures to suit particular applications. Such compositions may be in the form of a lozenge, tablet, toffee, nougat, chewy candy, chewing gum, capsule, liquid, gel, and the like. The pharmaceutically acceptable carriers may be selected from a wide range of materials. Without being limited thereto, such materials include diluents, binders and adhesives, lubricants, disintegrants, colorants, flavorings, sweeteners and miscellaneous materials such as buffers and adsorbents in order to prepare a particular medicated composition.

The preparation of confectionery and chewing gum products useful in the invention is historically well known and has changed very little over the years. Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

Hard boiled candy lozenges are prepared from a mixture of sugar and other carbohydrates that are kept in an amorphous or glassy condition. This form can be considered a solid syrup of sugars generally having from 0.5 to 1.5% moisture. Such materials normally contain up to 92% corn syrup, up to 55% sugar and from 0.1% to 5.0% water. The syrup component generally is prepared from corn syrups high in fructose, but may include other materials. Further ingredients such as flavorings, sweeteners, acidulents, colorants and so forth may also be added. In contrast, compressed tablet lozenges contain particular materials and are formed into structures under pressure. They generally contain sugars in amounts up to 95% and typical tablet excipients such as binders and lubricants as well as flavors, colorants and so forth.

Lozenges may also be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7 g/cc.

The high boiling syrup component, or "bob syrup", is relatively viscous, possesses a higher density than the frappe, and frequently contains a substantial amount of sugar. Conventionally, the final nougat composition is prepared by the addition of the "bob syrup" to the frappe under agitation, to form the basic nougat mixture. Further conventional ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONARY:* Science and Technology, 2nd edition, AVI Publishing Co., Inc., Westport, Conn., (1980), at Pages 424–425.

The delivery system may be incorporated into pharmaceutical tablets which are designed to be chewed or swallowed whole. The chewable form is particularly advantageous because of convenience, patient acceptance and rapid onset of bioactivity. Such factors as the amount of active substance per tablet, flavor, compressibility characteristics and organoleptic properties of the drug must be considered to insure acceptable stability and quality as well as good taste and mouthfeel.

The preparation of chewable medicated candy is prepared by procedures similar to those used to make soft confectionary. This procedure generally involves the formation of a boiled sugar-corn syrup blend to which is added a frappe mixture. The boiled sugar-corn syrup blend may be prepared from sugar and corn syrup blended in parts by weight ratio of 90 to 10:10 to 90. This blend is heated to temperatures above 250° F. to remove water and to form a molten mass. The frappe is generally prepared from gelatin, egg albumen, milk proteins such as casein, and vegetable proteins such as soy protein and the like, which are added to a gelatin solution and rapidly mixed at ambient temperature to form an aerated sponge like mass. The frappe is then added to the molten candy base and mixed until homogeneous at temperatures between 150° F. and 250° F. The composite can then be added as the temperature of the mix is lowered below the melting point of the matrix, whereupon additional ingredients are added flavors, and colorants are added. The formulation is further cooled and formed to pieces of desired dimensions.

A general discussion of pharmaceutical and confectionery vehicles may be found in H. A. Lieberman and L. Lachman, *Pharmaceutical Dosage Forms: Tablets* Volumes 1-3, Marcel Dekker, Inc., New York, N.Y. at pages 289 to 466.

Chewing gum formulations in which the novel delivery system may be employed, will vary greatly depending on various factors such as the type of base used, consistency desired and other components used to make the final product. In general, useful amounts of gum base vary from about 5% to about 45% by weight of the final chewing gum composition, with preferred amounts being about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of $\alpha$-pinene or $\beta$-pinene; terpene resins including polyterpene and mixtures thereof. The solvent may be employed in an amount ranging from about 10% to about 75% and preferable about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may also include the conventional additives such as flavoring agents, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance when auxiliary sweeteners are utilized in a particular vehicle, the present invention contemplates the inclusion of those sweeteners well known in the art, including both natural and artificial sweeteners. Thus, additional sweeteners may be chosen from the following non-limiting list: sugars such as sucrose, glucose (corn syrup), dextrose, invert sugar, fructose, and mixtures thereof; saccharine and its various salts such as the sodium or calcium salt; cyclamic acid and its various salts such as the sodium salt; the dipeptide sweeteners such as aspartame; dihydrochalcone; glycyrrhizin;

*Stevia rebaudiana* (Stevioside); and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Reissue Pat. No. 26,959. Also contemplated is the synthetic sweetener 3,6-dihydro-6-methyl-1-1,2,3oxathiazin-4-one-2,2-dioxide particularly the potassium (Acesulfame-K), sodium and calcium salts thereof as described in German Patent No. 2,001,017.7.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition weight.

The colorants useful in the present invention, includes the pigments such as titanium dioxide, that may be incorporated in amounts of up to about 1% by weight, and preferably up to about 6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857-884, which text is accordingly incorporated herein by reference.

Figure 1:
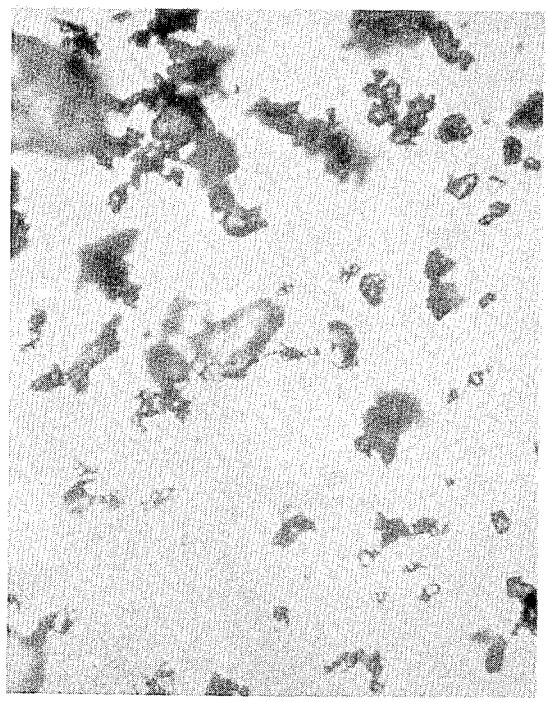
FIG. 1 is a magnified (125×) photograph of crystalline particles of potassium chloride. The irregular shape and size along with the sharp edges are apparent. These characteristics, as discussed herein, make the particles difficult to uniformly coat.
Figure 2:
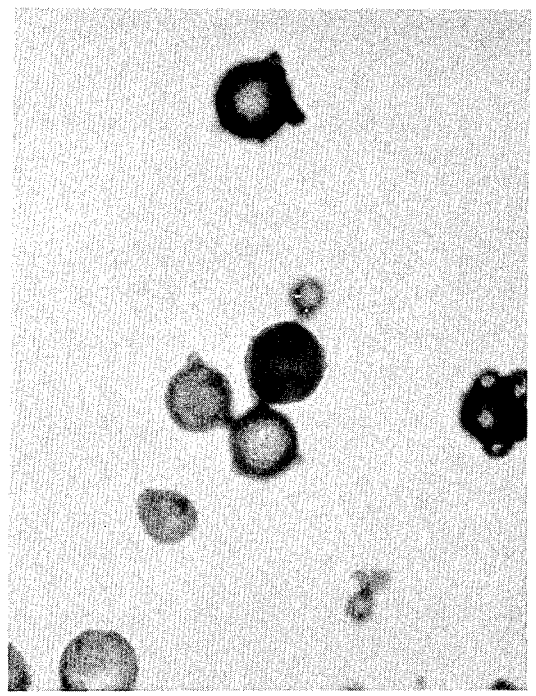
FIG. 2 is a magnified (125×) photograph of the inventive delivery system. The spherical shape is evidence of the uniformity in coating that the hydrophobic matrix provides for the drug core. The spherical agglomerates in this photograph are approximately 60 U.S. standard mesh. Potassium chloride is the drug contained within the hydrophobic matrix coating. It is apparent that the physical surface characteristics of the potassium chloride have been substantially modified to provide a temporary moisture barrier to prevent hydration and subsequent unpleasant taste in the mouth.

The following examples serve to provide further appreciation of the invention but are not meant in any way to restrict the effective scope of the invention. All percentages throughout the specification are by weight % of the final delivery system unless otherwise indicated.

EXAMPLE ONE

This example demonstrates the preferred composition and method of preparation. A mixture of about 61 to about 80% hydrogenated palm oil, and about 0.5 to about 30% monoglyceride were melted at a temperature of about 85° C. To this mixture 0.5 to about 20% lecithin was added and mixed until it dissolved. At this point the mixture is homogeneous. Next about 10 to about 20% of KCl (60 mesh) is added and mixed at high shear to obtain a uniform dispersion of the drug. The molten mixture is then fed into a warm spray nozzle and sprayed under controlled pressure to obtain a particle droplet size of about 200 to about 30 U.S. standard mesh. Particles outside this size range were screened out. The droplets congealed upon contact with the cooler atmosphere, forming a dry powder material. This powder is the agglomerate referred to herein. At this point, about 5 to about 15% sweetener may optionally be mixed in with the agglomerate. The agglomerate is then coated with a molten mixture of 1275 grams of hydrogenated palm oil and 225 grams of paraffin wax using standard fluidized bed granulation techniques. A Glatt GPC-15 fluidized bed granulator is used. The inlet temperature of the molten mixture is about 55° to about 65° C. and the outlet temperature is about 35° to about 40° C. The rate of spray is about 80 milliliters per minute at a pressure of about 3 bar. The spray is directed into a stream of agglomerate suspended in an apparatus that creates a strong upward air current in which the sweetener moves. The stream of agglomerate passes through a zone of the finely atomized droplets of the molten coating material, after which the thus coated agglomerates pass out of the upward stream and pass downward in a fluidized condition counter current to the flow air whereupon they are dried, and may reenter the upward moving coating zone for a subsequent discrete coating application.

EXAMPLE TWO

Example one was repeated substituting about 5% to about 15% of cholestyramine in place of KCl.

EXAMPLE THREE

Example one was repeated using about 4 to about 10% pseudophedrine HCl in place of KCl. When judged by an expert panel, the resulting delivery system did not exhibit the typical bitter and astringent taste of the drug.

EXAMPLE FOUR

Example one was repeated substituting about 4 to about 10% dextromethorphan for the KCl. When judged by an expert panel, the resulting delivery system did not exhibit the bitter and astringent taste of the drug.

EXAMPLE FIVE

Example two was repeated using about 40% of cholestyramine in place of KCl.

EXAMPLE SIX

Example One was repeated substituting about 4 to about 15% pseudophedrine for the KCl. An expert panel judged the resulting delivery system to be free of the unpleasant taste commonly associated with the drug.

EXAMPLE SEVEN

This example is intended to demonstrate the use of the inventive delivery system in a liquid drink.

The delivery system was prepared as follows. A mixture was prepared by combining about 20% of hydrogenated palm oil with about 25% distilled monoglyceride at a temperature of about 80°–90° C. To this mixture is added about 17% lecithin and mixed until the emulsifier is dissolved. Mixing should be continued until homogeneity is achieved. Next about 8% aspartame is mixed in, followed by about 30% powdered KCl (100 mesh), and mixing is continued to obtain a uniform dispersion of the drug. The molten mixture is then fed into a spray nozzle and sprayed under a controlled pressure to obtain a particle-droplet size of about 50 to about 100 U.S. standard mesh. The droplets congealed upon contact with the cooler atmosphere, forming a dry powder. The particles of power constitute the inventive agglomerate.

A second agglomerated material was prepared using the following procedures. About 79% of powdered locust bean gum was dry blended with about 10% of granular citric acid, about 8% microcrystalline cellulose, about 0.2% FD & C Yellow #5, about 0.1% FD & C Yellow #6, about 0.8% sodium saccharin and about 0.8% aspartame. This dry mixture is then fluidized in a stream of air and sprayed with a 1.5% aqueous solution of carboxymethyl cellulose. The result of the spraying yielded aggregates of the dry blended particles, the particles being partially coated and bound together with carboxymethyl cellulose.

The aggregates were dried and dry mixed with the inventive agglomerates containing KCl. Flavor (3 grams) and dextrose (8 grams) were then added to this final mixture. About 10 grams of this final mixture was placed in about 6 to 8 ounces of water and stirred. The resultant dispersion was free of lumps or caking. When judged by an expert panel, the drink exhibited a pleasant taste, free of the bitterness associated with potassium chloride.

The invention being thus described, it will be obvious that the same may be varied in many ways. Such variations are not to be regarded as a departure from the spirit and scope of the invention and all such modifications are intended to be included within the scope of the following claims.

What is claimed is:

1. A dry particulate drug delivery system designed to be chewed or swallowed whole comprising:

(A) an antitussive in an amount of about 1% to about 75%; and (B) a hydrophobic matrix comprising (i) about 0.5% to about 20% by weight of an emulsifier; and (ii) about 61% to about 95% by weight of an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; and (iii) at least one glyceride, wherein the antitussive and hydrophobic matrix form an agglomerate, and (C) a coating surrounding said agglomerate effective to delay hydration until ingested comprising about 200% to about 400% by weight of the agglomerate an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; wherein the coating forms a protective barrier effective to prevent unpleasant taste perception for the antitussive agglomerate.

2. The delivery system of claim 1 wherein the emulsifier is lecithin.

3. The delivery system of claim 1 wherein the fatty acid is selected from the group consisting of hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil and mixtures thereof.

4. The delivery system of claim 3 wherein the fatty acid is present in amounts of about 61% to about 95% by weight of the delivery system.

5. The delivery system of claim 3 wherein the fatty acid is refined hydrogenated palm oil present in amounts of about 63% to about 90% by weight of the delivery system.

6. The delivery system of claim 1 wherein the glyceride is present in amounts of about 0.5% to about 20% by weight of the delivery system.

7. The delivery system of claim 6 wherein the glyceride is a distilled monoglyceride present in amounts of about 1% to about 3% by weight of the delivery system.

8. The delivery system of claim 6 wherein the emulsifier is lecithin, present in amounts of about 0.5% to about 9%.

9. The delivery system of claim 3 having a melting point in the range of about 25° C. to about 90° C.

10. The delivery system of claim 1 having a particle size of about 200 to about 30 U.S. Standard mesh size.

11. A dry particulate composite having a substantially hydrophobic exterior designed to be chewed or swallowed whole comprising (A) an agglomerated mixture of about 1% to about 75% of an antitussive and a matrix wherein the matrix comprises:

(i) about 0.5% to about 20% fat soluble lecithin;

(ii) about 61% to about 90% of an edible material having a melting point in the range of about 25° C. to about 100° C. selected from the group consisting of (a) a fatty acid having an iodine value of about 1 to about 10; (b) natural waxes; (c) synthetic waxes; (d) and mixtures thereof;

(iii) about 0.5% to about 30% of a glyceride;

said composite having a melting point in the range of about 20° C. to about 90° C.

12. The composite of claim 11 contained in a confectionary product.

13. The composite of claim 11 contained in a chewing gum product.

14. The composite of claim 11 contained in a pharmaceutical preparation.

15. The delivery system of claim 1 wherein the antitussive is selected from the group consisting of dextromethorphan, dextromethorphan hydrobromide, noscapine, carbetapentane citrate and chlophedianol hydrochloride.

16. The delivery system of claim 1 wherein the antitussive is dextromethorphan.

17. The composite of claim 11 wherein the antitussive is selected from the group consisting of dextromethorphan, dextromethorphan hydrobromide, noscapine, carbetapentane citrate and chlophedianol hydrochloride.

18. The composite of claim 11 wherein the antitussive is dextromethorphan.

19. A method of preparing the dry particulate drug delivery system of claim 1 comprising:

A. Formation of an agglomerate of the antitussive and the hydrophobic matrix comprising the steps of melting the hydrophobic matrix and dispersing the antitussive uniformly therein; feeding the dispersion under controlled pressure to maintain the particle size between about 200 to about 30 mesh, collecting the agglomerate; and B. Coating the agglomerate by conducting the agglomerate through a stream of air passing through a zone of atomized droplets of a second hydrophobic material.

20. The method of claim 19 wherein said antitussive is selected from the group consisting of dextromethorphan, dextromethorphan hydrobromide, noscopine, carbetapentane citrate and chlophedianal hydrochloride.

21. The method of claim 20 wherein the antitussive is dextromethorphan.

* * * * *